US009547000B2

(12) United States Patent
Gravel-Lacroix et al.

(10) Patent No.: US 9,547,000 B2
(45) Date of Patent: Jan. 17, 2017

(54) CHROMOGENIC ABSORBENT MATERIAL FOR ANIMAL LITTER AND RELATED CHROMOGENIC SOLUTION

(71) Applicant: 7905122 CANADA INC., Boucherville, Quebec (CA)

(72) Inventors: Marie-Cleo Gravel-Lacroix, Quebec (CA); Paul Jollez, Quebec (CA); Isabelle Bolduc, Quebec (CA)

(73) Assignee: 7905122 Canada Inc., Quebec (CA)

( * ) Notice: Subject to any disclaimer, the term of this patent is extended or adjusted under 35 U.S.C. 154(b) by 0 days.

(21) Appl. No.: 14/424,929

(22) PCT Filed: Mar. 14, 2013

(86) PCT No.: PCT/CA2013/050195
§ 371 (c)(1),
(2) Date: Feb. 27, 2015

(87) PCT Pub. No.: WO2014/032175
PCT Pub. Date: Mar. 6, 2014

(65) Prior Publication Data
US 2015/0233899 A1 Aug. 20, 2015

Related U.S. Application Data

(60) Provisional application No. 61/694,508, filed on Aug. 29, 2012.

(51) Int. Cl.
*G01N 33/52* (2006.01)
*A01K 1/015* (2006.01)
*G01N 33/543* (2006.01)
*C12Q 1/28* (2006.01)

(52) U.S. Cl.
CPC .......... *G01N 33/526* (2013.01); *A01K 1/0152* (2013.01); *G01N 33/543* (2013.01); *C12Q 1/28* (2013.01)

(58) Field of Classification Search
CPC .. G01N 33/526; G01N 33/543; A01K 1/0152; C12Q 1/28
USPC ....................................... 119/171
See application file for complete search history.

(56) References Cited

U.S. PATENT DOCUMENTS

| 4,460,684 | A | * | 7/1984 | Bauer ................. C12Q 1/54 435/14 |
| 4,615,923 | A | | 10/1986 | Marx |
| 4,883,021 | A | | 11/1989 | Ducharme et al. |
| 5,760,121 | A | | 6/1998 | Beall |
| 6,042,839 | A | | 3/2000 | Lahanas |
| 6,197,849 | B1 | | 3/2001 | Zilg |
| 6,228,903 | B1 | | 5/2001 | Beall |
| 6,261,640 | B1 | | 7/2001 | Pinnavaia |
| 6,271,297 | B1 | | 8/2001 | Ishida |
| 6,376,034 | B1 | | 4/2002 | Brander |
| 6,399,690 | B2 | | 6/2002 | Lan |
| 6,407,155 | B1 | | 6/2002 | Qian |
| 6,414,069 | B1 | | 7/2002 | Pinnavaia |
| 6,521,690 | B1 | | 2/2003 | Ross |
| 6,579,927 | B1 | | 6/2003 | Fischer |
| 6,586,500 | B2 | | 7/2003 | Bagrodia |
| 6,730,719 | B2 | | 5/2004 | Powell |
| 7,533,630 | B2 | * | 5/2009 | Steckel ................ A01K 1/0152 119/165 |
| 2002/0165305 | A1 | | 11/2002 | Knudson, Jr. |
| 2002/0169246 | A1 | | 11/2002 | Barbee |
| 2003/0060555 | A1 | | 3/2003 | Lorah |
| 2003/0134942 | A1 | | 7/2003 | Lee |
| 2003/0170905 | A1 | * | 9/2003 | Kamyshny ........... A01K 1/0152 436/164 |
| 2008/0022940 | A1 | * | 1/2008 | Kirsch ................ A01K 1/0152 119/173 |

FOREIGN PATENT DOCUMENTS

| CA | 2308537 | 11/2000 |
| CA | 2352502 | 1/2002 |
| CA | 2462053 | 9/2004 |
| CA | 2607758 | 5/2008 |

(Continued)

OTHER PUBLICATIONS

Okada, et al., Mat. Res. Soc. Proc., 1990, 171, 45-50.
Reis, et al., J. Adv. Polym. Technol. 1997, 16, 263.
DeCarvalho, et al., Carbohydr. Polym. 2001, 45(2), 189-194.
Park, et al., Macromolecular Materials and Engineering, 2002, 287(8), pp. 553-558, J. of Mat. Sci, 2003, 38 (5), pp. 909-915.
McGlashan, et al., Polymer international, 2003, 52(11), pp. 1767-1773.

(Continued)

*Primary Examiner* — Korie H Chan
(74) *Attorney, Agent, or Firm* — Brinks Gilson & Lione

(57) ABSTRACT

A chromogenic absorbent material and related chromogenic solution, use, process and application for an animal litter. The chromogenic absorbent material includes an absorptive material for absorbing an animal excretion; an oxidizing agent responsive to peroxidatic/pseudoperoxidatic activity in the animal excretion to provide oxidizing activity; and an inclusion complex including a host compound and a guest compound, the guest compound being a chromogenic indicator associated with the host compound and being chromogenically responsive to the oxidizing activity of the oxidizing agent. The chromogenic absorbent material may be prepared from the chromogenic solution including the oxidizing agent and the inclusion complex. The chromogenic absorbent material may be used as particles combined with animal litter for detection of peroxidatic/pseudoperoxidatic activity in the animal excretion. The chromogenic material or solution may include a buffering agent, a colour enhancer, a stabilizer or a metal-scavenger agent or a combination thereof.

21 Claims, 6 Drawing Sheets

(56) References Cited

FOREIGN PATENT DOCUMENTS

| CA | 2737489 | 11/2010 | | |
|----|---------|---------|---|---|
| CA | WO 2010133001 A1 * | 11/2010 | ........... | A01K 1/0152 |
| EP | 1203789 | 5/2002 | | |
| EP | 1327435 | 7/2003 | | |
| JP | 01-296933 | 10/2001 | | |
| JP | 02-203936 | 7/2002 | | |
| JP | 09-187493 | 8/2009 | | |
| WO | 2004043663 | 5/2004 | | |

OTHER PUBLICATIONS

Darder, et al., Chemistry of materials, 2003, 15 (20), pp. 3774-3780.
Li, et al., Radiation physics and chemistry, 2004, 69(6) Apr, pp. 467-471.
Zhang, Sichun, et al. "β-Cyclodextrin Sensitized Chemiluminescence of Hemoglobin-Hydrogen Peroxide-Carbonate and its Analytical Application", *Analytica Chimica Acta*, vol. 475 (2003), pp. 163-170.
International Search Report for PCT/CA2013/050195, dated Jun. 17, 2013.

\* cited by examiner

CHROMOGENIC ABSORBENT MATERIAL FOR ANIMAL LITTER AND RELATED CHROMOGENIC SOLUTION

This application is a National Stage application of International Application No. PCT/CA2013/050195, filed Mar. 14, 2013. This application also claims priority to U.S. Provisional Application Ser. No. 61/694,508, filed Aug. 29, 2012.

FIELD OF THE INVENTION

The present invention relates to the field of animal blood detection and more particularly to animal litter including chromogenic absorbent material for detecting animal blood.

BACKGROUND OF THE INVENTION

Domestic animals such as cats are susceptible to various diseases, ailments and conditions, which are not only arduous and painful for the animal itself but also a source of concern and stress for animal owners. While animal owners nurture, watch over and bestow affection on their pets, they must balance this attention with other responsibilities. Convenience is thus an important factor when taking care of a domestic animal. While owners may be devoted and considerate to their pets, they may lack the sophistication to diagnose animal diseases, ailments and conditions. Convenient, simple and effective means to inform pet owners of the presence of diseases, such as urinary infections, are desired so that appropriate steps can be taken to reverse, mitigate or avoid serious illness in the animal.

For example, feline urinary tract disease can be a serious condition for cats. In feline urinary tract disease, crystals of magnesium ammonium phosphate can precipitate in the cat's urinary tract and cause obstruction. If untreated, the obstruction can lead to intense pain and can often be fatal within days. In some cases, upon observing feline urinary tract disease symptoms—such as bloody urine and urination discomfort and straining—cat owners often consult their veterinarian who may be able to provide treatments, which may be expensive. However, many cats with feline urinary tract disease do not show any obvious symptoms, which is why this disease has been referred to as a "silent killer".

Early detection of feline urinary tract disease is therefore of paramount importance in facilitating treatment, lessening the likelihood of severe complications or aggravations, and reducing the cost of treatment.

Some methods of early detection are known. Early detection may be possible by occult blood testing, allowing animal owners to treat the problem of urinary tract disease by changing the animals' diets. However, some known occult blood testing techniques present various disadvantages concerning the complexity and inconvenience of the tests. For instance, animals will often resist urine sample gathering.

It is known to use diagnostic agents, incorporated into test strips, beads or particles, for detection purposes. Usually, such test strips consist of an absorbent carrier made from fibrous or non-woven material, in the simplest case filter paper, which is coated or impregnated with the detection reagents. Components of the detection reagent may be a chromogen as an indicator, an oxidizing agent such as a hydroperoxide as an oxidizer of the indicator. The oxidizing agent is sometimes also called a sensitizer or an accelerator. Standard additional components are, apart from a surface-active agent (wetting agent), thickening agents which prevent the bleeding of the wetted test field, pigments, complex-forming agents and/or other stabilizers for the chromogen and/or the hydroperoxide.

Similarly, various analytical methods are presently available for detecting the presence of "peroxidatively active substances" in samples such as urine, fecal suspensions, and gastrointestinal contents. According to U.S. Pat. No. 4,460,684, hemoglobin and its derivatives are typical of such peroxidatively active substances because they behave in a manner similar to the enzyme peroxidase. Such substances are also referred to as pseudoperoxidases. Peroxidatively active substances are enzyme-like in that they catalyze the redox reaction between peroxides and benzidine, o-tolidine, 3,3',5,5'-tetramethylbenzidine, 2,7-diaminofluorene or similar benzidine-type indicator substances, thereby producing a detectable response such as a color change. Most methods for determining the presence of occult blood in test samples rely on this pseudoperoxidatic activity. A benzidine-type indicator responds in the presence of hydroperoxide and peroxidase by changing its light absorptive capability.

Providing a reliable occult blood detection system in animal litter itself also has many problems and challenges. For example, the test indicator material should be stable when exposed to a wide variety of ambient conditions, be they dry or humid, and over a wide range of temperatures. Such stability is quite often difficult to achieve.

A further problem with many known test indicators is that pet owners are insufficiently observant or sophisticated to appreciate the positive indication, such as a color change, before the indicator decays. Many known indicators do not stay at the changed color for a sufficient period of time to allow pet owners to reliably recognize the indicated health issue.

An additional problem with various detection reagents mixed with animal litter is that the test reagents give off sufficient scent such that cats, which have an extraordinary sense of smell, recognize the odor change in their litter and thus tend to shy away from the litter. As will be appreciated, this not only defeats the purpose of a convenient detector but can also cause unwanted excretory mishaps. Thus, test reagents with significant, offensive or upsetting odors—both to the user and the cat—have many disadvantages.

A further problem with known detection reagents is poor shelf life stability, particularly if combined with an animal litter for storage as a single mixture. Poor stability leads to disadvantages in the ability to store, transport, display, purchase and use the detection-litter combination.

Detection materials that are merely coated over the surface of a carrier material also have various disadvantages that may relate to poor shelf-life stability, low in-use stability and lifetime, and insufficient color change visibility.

Known materials and methods for detection of animal excretion tract disease have involved one or more of the above deficiencies.

Some detection methods are disclosed in WO 2010133001 (Jollez et al.) which describes a chromogenic composite material for use with animal litter. The composite material can include an absorptive polymer material; clay; a chromogenic indicator; and an oxidizing agent that is available and responsive to peroxidase or pseudoperoxidase activity in the feline urine to activate the chromogenic indicator. The chromogenic indicator may be 3,3',5,5'-tetramethylbenzidine, also referred to as TMB.

As for TMB, it is an electron donor that can reduce hydrogen peroxide in presence of peroxidase enzyme. In ambient conditions, TMB may be present as a white crystal powder that is only slightly soluble in aqueous solutions.

Organic solvents may therefore have been preferred to solubilize TMB for applications.

Despite the developments in detection methods for animal excretion tract disease, there is still a need for an improved technology. In order to improve solubility of TMB in water, water soluble inclusion complexes have been employed in certain fields.

SUMMARY

The present invention responds to the above need by providing various techniques including a chromogenic absorbent material, a chromogenic solution, use and processes of manufacture.

In one aspect, there is provided a chromogenic absorbent material for an animal litter. The chromogenic absorbent material includes:
an absorptive material for absorbing an animal excretion;
an oxidizing agent responsive to peroxidatic/pseudoperoxidatic activity in the animal excretion to provide oxidizing activity; and
an inclusion complex including a host compound and a guest compound, the guest compound being a chromogenic indicator associated with the host compound and being chromogenically responsive to the oxidizing activity of the oxidizing agent.

In an optional aspect, the oxidizing agent and the inclusion complex may be distributed on at least an exterior surface of the absorptive material. Optionally, the oxidizing agent and the inclusion complex may be distributed within the absorptive material. Optionally, the inclusion complex may be distributed within a sub-surface region of the absorptive material so as to be exposable upon absorption of the animal excretion.

In another optional aspect, the absorptive material may include a polymeric material. Optionally, the polymeric material may include starch, modified starch, amylopectin, modified amylopectin, amylose, modified amylose, cellulose or cellulosic fibers or a combination thereof. Optionally, the starch may include starch granules, pre-gelatinized starch, glass-like starch, waxy starch, anionic starch, cationic starch, fractionated starch, cross-linked starch, hydroxyalkylated starch or alkylated starch or a combination thereof. Further optionally, the cellulose or cellulosic fibers may be derived from paper, recycled paper, paper sludge or refined pulp or a combination thereof. The refined pulp may include wood pulp or a pulp of vegetal origin.

In another optional aspect, the chromogenic indicator may be responsive to the oxidizing agent by turning blue in presence of the peroxidatic/pseudoperoxidatic activity in the animal excretions.

In another optional aspect, the chromogenic indicator may be provided with a concentration and distribution within the absorptive material such that the chromogenic absorbent material turns to different shades of blue depending on an activity level of the peroxidatic/pseudoperoxidatic activity in the animal excretion.

In some embodiments, the chromogenic absorbent material may turn to:
light blue when the animal excretion has a blood concentration between about 0.0001% and about 0.0005%,
medium blue when the animal excretion has a blood concentration between about 0.0005% and about 0.09%, and
dark blue when the animal excretion has a blood concentration of at least 0.09%.

In another optional aspect, the chromogenic absorbent material may turn to blue in presence of the peroxidatic/pseudoperoxidatic activity after a contact time with the animal excretion between about 1 min and about 30 min.

In another aspect, there is provided a use of an inclusion complex in an animal litter for chromogenic indication of peroxidatic/pseudoperoxidatic activity in an animal excretion. The inclusion complex includes:
a host compound, and
a guest compound, the guest compound being a chromogenic indicator associated within the host compound, and the chromogenic indicator being chromogenically responsive to an oxidizing activity of an oxidizing agent.

In another aspect, there is provided a chromogenic solution for chromogenic indication of peroxidatic/pseudoperoxidatic activity in animal excretions. The chromogenic solution includes
a solvent;
an oxidizing agent responsive to the peroxidatic/pseudoperoxidatic activity in the animal excretions to provide oxidizing activity; and
an inclusion complex soluble in the solvent and including a host compound and a guest compound, the guest compound being a chromogenic indicator associated within the host compound, and the chromogenic indicator being chromogenically responsive to the oxidizing activity of the oxidizing agent.

In an optional aspect, the solution may have a mass ratio of total weight of host compound over total weight of chromogenic indicator between about 5 and about 60.

In an optional aspect, the solution may have a molar ratio of total moles of host compound over total moles of chromogenic indicator between about 1/10 and about 1/1.

In an optional aspect, the solution may have a mass concentration of oxidizing agent between about 0.1 wt % and about 0.5 wt %.

In an optional aspect, the solution may have a mass concentration of inclusion complex between about 1 wt % and about 50 wt %.

In an optional aspect, the solution may include a buffering agent so as to maintain a pH of the chromogenic solution between 5 and 7.

In an optional aspect, the solution may include a colour enhancer, a stabilizer or a metal-scavenger agent or a combination thereof.

In another aspect, there is provided a process for preparing a chromogenic solution for chromogenic indication of peroxidatic/pseudoperoxidatic activity in animal excretions. The process includes the steps of:
preparation of a base solution by addition of a host compound into a solvent;
addition of a chromogenic agent to the base solution so as to form a solvent-soluble inclusion complex including the host compound and the chromogenic agent as a guest compound associated within the host compound; and
addition of an oxidizing agent to the base solution to form the chromogenic solution, the oxidizing agent being capable of oxidizing the chromogenic agent in presence of the peroxidatic/pseudoperoxidatic activity in animal excretions to provide oxidizing activity, the chromogenic agent being chromogenically responsive to the oxidizing activity of the oxidizing agent.

In an optional aspect, the inclusion complex may be water-soluble. Optionally, the chromogenic indicator may include a benzidine-type compound including 3,3',5,5'-tetramethylbenzidine.

In another optional aspect, the host compound may include a polysaccharide. Optionally, the polysaccharide may include an oligosaccharide. Optionally, the oligosaccharide may include a cyclic oligosaccharide including hydroxypropyl-alpha-cyclodextrin, 2-hydroxypropyl-beta-cyclodextrin or hydroxypropyl-gamma-cyclodextrin or a combination thereof. Optionally, the oligosaccharide may also include a branched oligosaccharide.

In another optional aspect, the oxidizing agent may include a hydroperoxide or a hydroperoxide precursor or a combination thereof. Optionally, the hydroperoxide may include cumene hydroperoxide or diisopropylbenzene dihydroperoxide or a combination thereof.

In another optional aspect, the chromogenic absorbent material may also include a buffering agent, a stabilizer, a metal scavenger agent or a color enhancer or a combination thereof. Optionally, the color enhancer may include 6-methoxyquinoline, lepidin, phenol derivatives, nitrobenzene, N-methylpyrrolidone or ethylene carbonate or a combination thereof. Optionally, the buffering agent may include citrate, sodium citrate, phosphate or acetate or a combination thereof. Optionally, the stabilizer may include ammonium molybate, polyethylene glycol, polyvinylpyrrolidone, polyethylene oxide or derivatives thereof or a combination thereof. Optionally, the metal-scavenger agent may include ethylenediaminetetraacetic acid (EDTA) or EDTA sodium salt or a combination thereof.

In another aspect, there is provided a use of the above defined chromogenic absorbent material as chromogenic particles in combination with animal litter.

In an optional aspect, the chromogenic particles may include pellets, granules, disks, squares according to their process of manufacture.

In another optional aspect, the chromogenic particles may have an exterior contact surface between about 19 $mm^2$ and about 400 $mm^2$, In another optional aspect, the chromogenic particles may have an average thickness between about 1 mm and about 10 mm.

In another optional aspect, the chromogenic particles may be distributed on a top surface of the animal litter. Alternately, the chromogenic particles may be substantially evenly distributed within the animal litter.

In another optional aspect, the animal litter may include clay based particles, cellulosic particles, perlite based particles, silica based particles, corn based particles, paper based particles or wheat based particles or a combination thereof.

In another aspect, there is provided a use of a chromogenic solution as defined above for application on at least an exterior surface of an absorptive material so as to form the chromogenic absorbent material as defined above.

In another aspect, there is provided particles of chromogenic absorbent material as defined above, the particles of chromogenic absorbent material being used in combination with or as animal litter.

In another aspect, there is provided an animal litter material for detecting peroxidatic/pseudoperoxidatic activity in an animal excretion, the animal litter material including the chromogenic absorbent material as defined above.

It should be understood that any one of the above mentioned aspects of each chromogenic absorbent material, chromogenic solution, related uses, process and applications may be combined with any other of the aspects unless two aspects clearly cannot be combined due to their mutual exclusivity. For example, the various structural elements of the chromogenic absorbent material described herein-above, herein-below and/or in the appended Figures, may be combined with any of the chromogenic solution, use of the chromogenic solution and processes descriptions appearing herein.

BRIEF DESCRIPTION OF THE DRAWINGS

Embodiments of the chromogenic absorbent material and related chromogenic solution, use and process according to the present invention are represented in and will be further understood in connection with the following figures.

Figure 1:
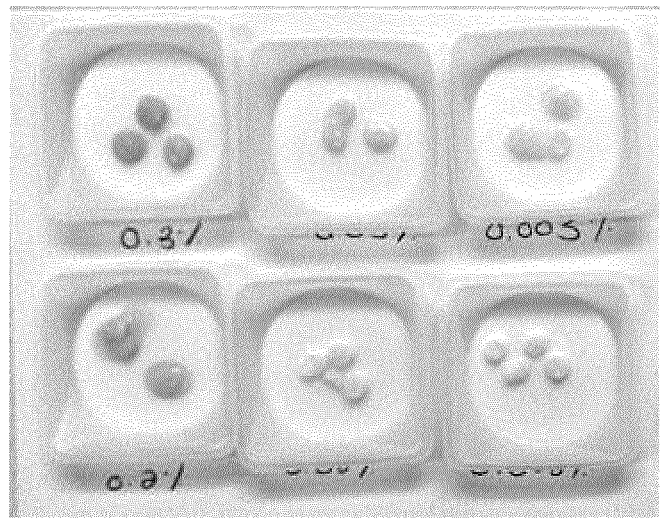
FIG. 1 is a photograph of six samples of wheat starch chromogenic particles after 2 minutes of contact with a diluted blood solution.

While the invention will be described in conjunction with example embodiments, it will be understood that it is not intended to limit the scope of the invention to such embodiments. On the contrary, it is intended to cover all alternatives, modifications and equivalents as may be included as defined by the present description. The advantages and other features of the present invention will become more apparent and be better understood upon reading of the following non-restrictive description of the invention, given with reference to the accompanying drawings.

DETAILED DESCRIPTION

The present invention provides a chromogenic solution and related chromogenic absorbent material for detecting blood in excretions. More particularly, the chromogenic absorbent material may be used in connection with an animal litter.

It should be understood that excretion refers to any matter excreted by an animal, such as urine or fecal matter. The chromogenic absorbent material may be used in any domestic animal litter including cat, dog litter and rodent litter. It may also be used for horse litter, cow litter or any other livestock litter. However, the present invention is not limited to detecting blood in animal excretions and may be used to detect blood in human excretions for example. The chromogenic solution may be applied to non-woven absorptive material, such as pads for this purpose.

In one aspect, the present invention relates to particles of chromogenic absorbent material that may be dispersed within the animal litter or at the surface of the animal litter.

In one aspect of the present invention, each particle of chromogenic absorbent material includes:
- an absorptive material;
- an oxidizing agent responsive to peroxidatic/pseudoperoxidatic activity in excretions; and
- an inclusion complex including a host compound and a guest compound, the guest compound being a chromogenic indicator associated within the host compound, and the chromogenic indicator being responsive to the oxidizing agent, the oxidizing agent and the inclusion complex being distributed on at least an exterior surface of the absorptive material.

It should be understood that the expression "the chromogenic indicator responsive to the oxidizing agent" means that the chromogenic indicator may change colour upon response of the oxidizing agent to peroxidase or pseudoperoxidase activity in excretions. Peroxidase or pseudoperoxidase are enzymes (hemoproteins) naturally present in blood and catalyzing the oxidation of peroxides, such as hydrogen peroxide, of a number of substrates such as ascorbate, ferrocyanide, cytochrome C and the leuco form of many dyes.

It should be understood that the expression "peroxidatic activity" refers to the ability of catalytic substances to drive the reaction of hydroperoxides with colorless chromogenic electron donors which become fluorescent or visibly colored after oxidation.

It should be understood that the expression "pseudoperoxidatic activity" refers to the ability of a peroxidase or a non-peroxidase catalytic substance to drive the reaction of hydroperoxidases with colorless chromogenic electron donors which become fluorescent or visibly colored after oxidation. Certain transition metals and their ions and hemoproteins are known to have pseudoperoxidatic activity. Basophils, neutrophils, eosinophils and mast cells synthesize endogenous peroxidase which can be visualized at the ultrastructural level in the secretory apparatus of immature cells. Red blood cells and hematin containing compounds have iron as part of their heme groups, which can catalyze the oxidation of chromogenic electron donors. This pseudoperoxidatic activity can be inhibited with strong $H_2O_2$ solutions, sodium azide and methanol-$H_2O_2$ solutions.

It should be understood that particle refers to any pellet, granule or piece of various shapes. Optionally, circular particles may have an average diameter ranging from 2.5 mm to 10 mm. Optionally, square or rectangular particles may have an average length ranging from 5 mm to 20 mm. Optionally, the particles may have a top surface ranging from 19 $mm^2$ to 400 $mm^2$ and a thickness ranging from 1 to 10 mm. The shape of the particles is conferred by their process of manufacture.

In an optional aspect, the absorptive material may be polymeric and optionally includes a polysaccharide, which provides polysaccharide chain backbones in addition to a general polysaccharide matrix. More particularly, polysaccharides may be starches, modified starches, amylopectin, modified amylopectin, amylose, modified amylose or mixture thereof. Amongst these polysaccharides, starch is frequently chosen as a polysaccharide for use in the agglomerated particle. Non-limiting examples of such starches are starch granules, pre gelatinized starches, glass-like starches, waxy starches, anionic starches, cationic starches, fractionated starches, cross-linked starches, hydroxyalkylated starches, alkylated starches and mixture thereof. Starch that is suitable for the present invention may be obtained from many sources, including but not limited to wheat, maize, buckwheat, potato, cassava, sorghum, millet, oat, arrowroot, barley, beans, peas, rice, rye, waxy starches and mixture thereof. A commonly used starch is wheat starch. Naturally occurring starch is usually organized in a semi-crystalline, water insoluble pattern, which is sometimes referred to as a "starch granule". The form of these starch granules is characteristic of their botanical origin, and their mean particle size may range from about 1 µm to about 60 µm. The absorptive material may also include cellulose or cellulosic fibers issued from paper, recycled paper or paper sludge. The cellulose might also be from refined pulp, such as wood pulp and from any vegetal origin, such as wheat, products derived from wheat, corn, products derived from corn, bamboo, pine wood, birch wood, poplar, eucalyptus or combination thereof. The absorptive material may optionally include perlite glass.

The oxidizing agent is reactive to peroxidatic/pseudoperoxidatic activity and is able to activate the chromogenic indicator contained in the inclusion complex. The oxidizing agent oxidizes the chromogenic indicator in presence of the enzymes peroxidase or pseudo-peroxidase. In an optional aspect, the oxidizing agent includes a hydroperoxide. Hydroperoxides may be, for example, cumene hydroperoxide which is suitable for detection of peroxidatic/pseudoperoxydatic activity. Additionally, cumene hydroperoxide can have some reactivity to elevated glucose levels.

Hydroperoxides are therefore suited for detection of urinary tract diseases. The hydroperoxide may also be, for example, diisopropylbenzene dihydroperoxide which has high selectivity to detection of peroxidatic/pseudoperoxydatic activity and thus of urinary tract disease. In an optional aspect, a combination of the previously mentioned hydroperoxides may be used in the chromogenic composition for selectively detecting several diseases in excretions. Optionally, the oxidizing agent may be a hydroperoxide precursor such as sodium percarbonate. Sodium percarbonate is a solid which decomposition forms hydrogen peroxide in presence of water.

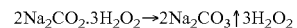

$$2Na_2CO_2.3H_2O_2 \rightarrow 2Na_2CO_3 \uparrow 3H_2O_2$$

It should be understood that "hydroperoxide" refers to compounds of the general formula, ROOH, wherein the R group is an aryl, alkyl, or acyl group (organic hydroperoxide), or hydrogen atom (hydrogen peroxide).

The oxidizing agent, triggered by the presence of peroxidatic/pseudoperoxidatic activity in excretions, oxidizes the chromogenic indicator which therefore changes of color. More particularly, the chromogenic indicator is an electron donor, i.e. a reducing agent that changes color upon losing an electron.

In an optional aspect, the host agent of the inclusion complex may be a cyclic oligosaccharide, such as hydroxypropyl-alpha-cyclodextrin, hydroxypropyl-beta-cyclodextrin (2HPβCD), hydroxypropyl-gamma-cyclodextrin or any combination thereof. The host agent of the inclusion complex may be a branched hydroxypropyl-beta-cyclodextrin or sulfobutyl-ether hydroxypropyl-beta-cyclodextrin sodium salt. Further details on the inclusion complex will be provided herebelow with description of embodiments of a chromogenic solution and related process of manufacture.

In an optional aspect, the chromogenic indicator may be a benzidine-type compound, i.e. a compound as shown in Formula I:

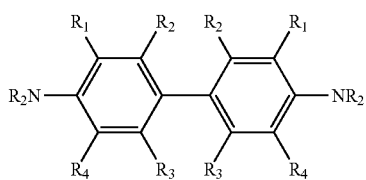

Formula I

In Formula I, groups $R_1$, $R_2$, $R_3$ and $R_4$ may be the same or different and may be hydrogen, halogen, a lower alkyl or alkoxy group containing 1 to 4 carbon atoms, a $(C_1\text{-}C_4)$-dialkylamino group, an acetylamino group, a nitro group or an aromatic group which may be substituted.

Optionally, the chromogenic indicator may be a compound as shown in Formula II:

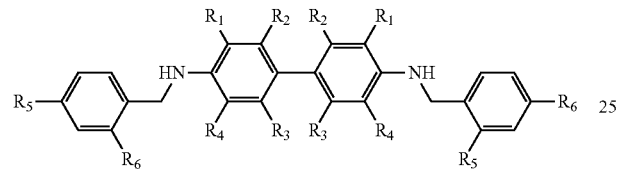

Formula II

In Formula II, groups $R_1$, $R_2$, $R_3$ and $R_4$ may be the same or different and represent hydrogen, halogen, and a lower alkyl or alkoxy group containing 1 to 4 carbon atoms, a $(C_1\text{-}C_4)$-dialkylamino group, an acetylamino group, a nitro group or an aromatic group which may be substituted; $R_5$ and $R_6$ are the same or different and represent water-soluble groups as hydroxyl groupl, amino group, acidic group, disulfonyl group, ether group, halogen, and a lower alkyl or alkoxy group containing 1 to 4 carbon atoms, a $(C_1\text{-}C_4)$-dialkylamino group, an acetylamino group or a nitro group.

Thus, a water soluble benzidine-type chromogenic indicator of Formula II, responds in the presence of hyperoxide and peroxidase by changing its light absorptive capability, which is due to the chemical transformation to the compound shown in Formula III:

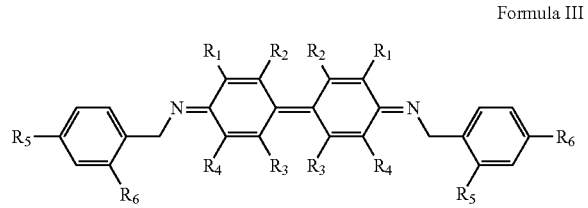

Formula III

Several different types of benzidine chromogenic indicators may be used in optional embodiments of the present invention.

Optionally, the chromogenic indicator may be 3,3',5,5'-tetramethylbenzidine (TMB). TMB is a colorless agent which turns blue upon oxidation. The peroxidase/pseudo-peroxidase enzymes catalyze the oxidation of TMB by the oxidizing agent (hydroperoxide) according to the following oxidation reaction:

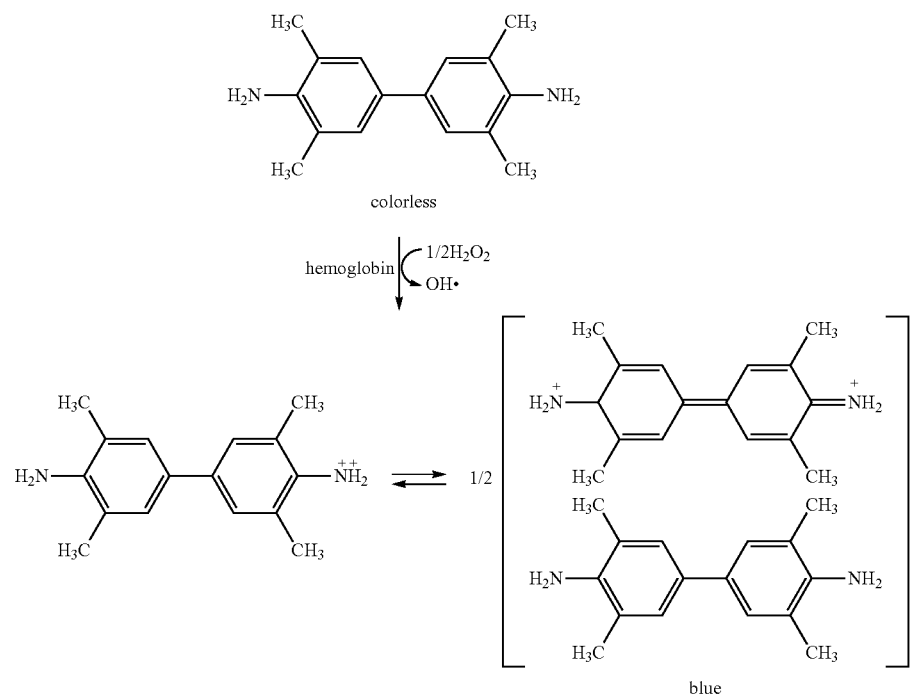

In an optional aspect, the chromogenic absorbent material may turn blue upon contact with excretions containing at least traces of blood (with therefore peroxidase/pseudo-peroxidase activity).

It should be understood that "blue" refers to any shade of blue. The chromogenic absorbent material may need a contact time with excretions sufficient to enable coloration. In an optional aspect, the particles may turn blue after a contact time ranging from about 1 min to about 30 min depending on the nature of the absorptive material of the particles.

In another optional aspect, the chromogenic absorbent material may turn to different shades of blue depending on the blood concentration in excretions. The intensity of the blue shade may be proportional to the blood concentration in excretions. The chromogenic absorbent material offers an easy and accurate blood test that may indicate the blood concentration in the excretions.

Figure 2:
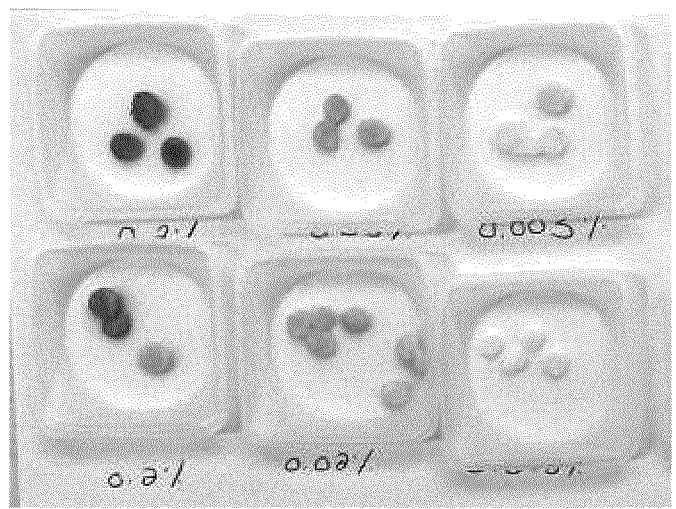
FIG. 2 is a photograph of six samples of wheat starch chromogenic particles after 45 minutes of contact with a diluted blood solution.

Experiments have been performed by depositing an aqueous blood solution of various blood concentrations on pieces of chromogenic absorptive paper and chromogenic pellets of wheat starch. The chromogenic absorptive paper has been prepared by spraying 100 g to 500 g of chromogenic solution per kg of absorptive paper. The chromogenic pellets of wheat starch have been prepared by extruding and heating wheat starch for gelatinization thereof with 0.2 to 1.2 kg of chromogenic solution per kg of wheat starch, optionally 0.3 to 0.5 kg. The extruded pellets were oven dried at 60° C. Several blood concentrations (volumic mass of blood per total volume of aqueous blood solution) were tested from 0.0001% to 1%. More particularly, referring to FIGS. 1 and 2, the aqueous blood solution is deposited on six groups of wheat starch pellets with respective blood concentration of 0.002% (volumic mass of blood per total volume of aqueous blood solution) 0.02%, 0.2%, 0.003%, 0.03% and 0.3%. FIG. 1 shows the six soaked groups of pellets after two minutes of contact time and FIG. 2 shows the same groups of pellets after forty-five minutes of contact time. Referring to FIG. 2, the groups of pellets have a blue color increasing in intensity with the blood concentration. The first group of pellets, soaked with a 0.002% concentrated blood solution, is not colored in blue. The change of color of the chromogenic indicator included in the pellets becomes discernible with a blood concentration of 0.003% after forty-five minutes. Comparison of FIGS. 1 and 2 shows that there is a minimum contact time to respect for observing a blue coloration of the soaked pellets. In FIG. 1, after two minutes of contact with the diluted blood solution, the pellets have not turned blue yet. In FIG. 2, after forty-five minutes, the pellets have their final blue shade. It should be noted that the intensity of the blue shades may decrease after height hours and turn greener.

Figure 3:
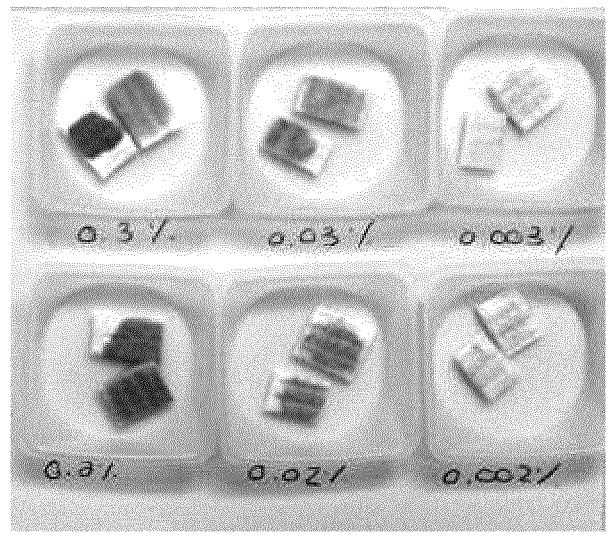
FIG. 3 is a photograph of six samples of paper chromogenic pieces after 2 minutes of contact with a diluted blood solution.
Figure 4:
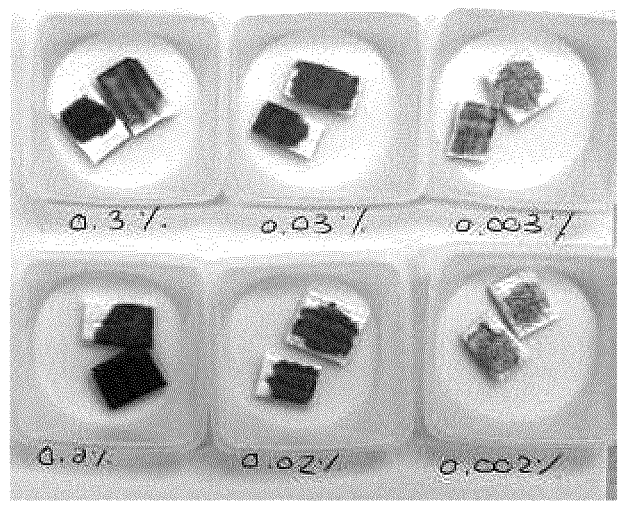
FIG. 4 is a photograph of six samples of paper chromogenic pieces after 45 minutes of contact with a diluted blood solution.

Referring to FIGS. 3 and 4, the aqueous blood solution is deposited on six groups of two paper absorbent pieces with respective blood concentration of 0.002%, 0.02%, 0.2%, 0.003%, 0.03% and 0.3%. FIG. 3 shows the six soaked groups of paper pieces after two minutes of contact time and FIG. 4 shows the same groups of paper pieces after forty-five minutes of contact time. The blue coloration already appears after two minutes of contact with the diluted blood solution. Especially, a blue coloration is observed for the first two pieces of paper absorbent soaked with a 0.002% concentrated blood solution. The chromogenic paper absorbent material is more efficient to detect traces of blood than the chromogenic wheat starch absorbent material. The characteristics of the absorptive material may be responsible for the difference in blood concentration threshold at which a blue coloration is observed. It may be explained by the porosity of the absorptive material: the contact surface of the chromogenic absorbent material increases with porosity of the material. For example, as wheat starch absorbent is less porous than paper absorbent, the contact surface available to excretions is insufficient to activate the chromogenic indicator so that a blue coloration is discernible at 0.02% blood concentration. The difference between paper coloration and wheat starch coloration may also be explained by the capillarity effect of paper, which enhances the penetration of urine in the paper and therefore contact more chromogenic indicator.

In an optional aspect, the nature and form of the absorptive material may be selected and modified to allow sufficient internal diffusion and retention of excretions to facilitate the chromogenic indicator response over time. For example, the absorptive material may be modified so as to increase its porosity. The chromogenic indicator may also be homogeneously dispersed throughout the absorptive material according to the preparation method of the chromogenic absorbent material. The chromogenic indicator may be present not only at the exterior surface of a given particle, but also in a neighboring sub-surface region that can be rapidly exposed to excretions that absorbs into the particle. Additionally, when the absorptive material is glassy or substantially transparent, the presence of the chromogenic indicator in a sub-surface region allows it to be readily visible when color change occurs and also avoids exposure to the air.

In an optional aspect, the chromogenic composition may further include a colour enhancer. Optionally, it may also include a buffering agent, a stabilizer, a metal scavenger agent or a combination thereof. The colour enhancer may optionally be 6-methoxyquinoline, lepidin, phenol derivatives, nitrobenzene, N-methylpyrrolidone, ethylene carbonate or any combination thereof. The buffering agent may optionally include citrate, sodium citrate, phosphate, acetate or any combination thereof. The stabilizer may optionally be ammonium molybate and derivatives thereof, polyethylene glycol, polyvinylpyrrolidone, polyethylene oxide and derivatives thereof, or combination thereof. The metal-scavenger agent may optionally be EDTA, EDTA sodium salt or any combination thereof.

Advantageously, the particles of chromogenic absorbent material offer an easy, reliable and efficient way to detect blood in animal excretion when used in combination with animal litter. Particles may be provided as a separate additive to animal litter for the purpose of being mixed to conventional animal litter when the animal excretions need to be tested. Particles may also be provided pre-mixed directly with conventional animal litter in a packaged litter formula for sale.

In another aspect, the present invention relates to a chromogenic solution including:
  a solvent;
  an oxidizing agent responsive to peroxidatic/pseudoperoxidatic activity in excretions;
  an inclusion complex soluble in the solvent and including a host compound and a guest compound, the guest compound being a chromogenic indicator associated within the host compound, and the chromogenic indicator being responsive to the oxidizing agent.

Optionally, the chromogenic solution may include a buffering agent so as to maintain a pH of the chromogenic solution between 5 and 7. Extreme pH may be avoided.

Optionally, the chromogenic solution may include a colour enhancer, a stabilizer, a metal-scavenger agent or a combination thereof as defined above.

In another aspect, the present invention relates to the use of the above-mentioned chromogenic solution for association with an absorptive material so as to form the chromogenic absorbent material.

It should be understood that each of the above-mentioned aspect in relation to the inclusion complex and oxidizing agent included in the chromogenic composition may be adapted to aspects of the inclusion complex and oxidizing agent included in the chromogenic solution.

In another aspect, the present invention relates to the use of an inclusion complex in animal litter for chromogenic indication of peroxidatic/pseudoperoxidatic activity in excretions. The inclusion complex includes a host compound and a guest compound associated within the host compound. The chromogenic indicator is the guest compound of the inclusion complex. The use of a host compound for association with the chromogenic indicator enables to form an inclusion complex which has a superior solubility in the solvent than the chromogenic indicator alone. Advantageously, a chromogenic indicator which was not soluble or not enough soluble into a specific solvent becomes soluble in that same solvent because of the inclusion complex acting as a vessel for the chromogenic indicator. For example, as TMB (chromogenic indicator) is slightly soluble in water, an inclusion complex can be formed with 2HPβCD (host compound), which is water-soluble. Aqueous solutions using water as solvent may therefore be used instead of organic solvents. The chromogenic solution may be therefore prepared without the use of organic solvent for the benefit of workers and environment. Indeed, organic solvents may cause environmental problems such as air pollution, water and soil contamination, as well as being harmful to wildlife. When preparing a solution with organic solvent, workers are also exposed to various hazards, such as risks of fire and poisoning, skin damage, eye injury and nervous system disorders. Animal may further dislike the odors of solvents and discourage them from using the litter.

Figure 5:
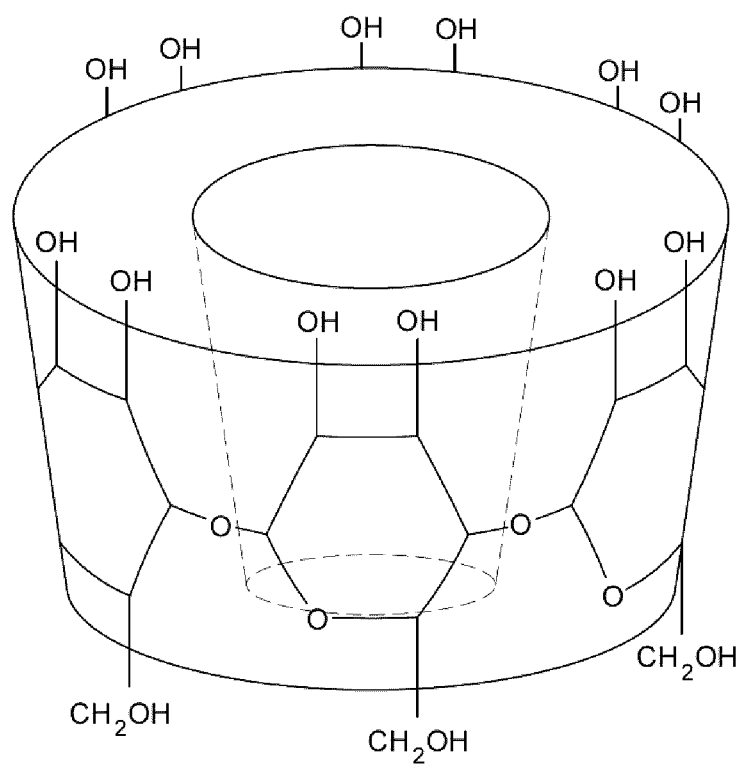
FIG. 5 is a scheme of a solubilizing agent (2-HPβCD).

Referring to FIG. 5, the 2HPβCD has a frusto-conical tridimensional configuration. The inner space of the frusto-conical configuration enables trapping and stabilizing the chromogenic indicator, TMB. An inclusion complex TMB-2-HPβCD may be formed and contributes to solubilize TMB into the solvent so as to form the chromogenic solution, which is applicable on the absorptive material.

The solubility of the inclusion complex TMB-2-HPβCD in non-organic solvent is about ten times greater compared to the solubility of isolated TMB. The following Table 1 presents results regarding the solubility of TMB in different solvents.

TABLE 1

| SOLVENT | SOLUBILITY (mM) |
|---|---|
| Dimethylsulfonamide | 1.6 |
| Methanol | 5.2 |
| Ethyl acetate | 10 |
| Water | 0.1 |

Consequently, the chromogenic absorbent material includes a higher concentration of inclusion complexes and is more color responsive when contacted by blood. Indeed, upon contact with blood in excretions, more TMB is available for oxidation and the color response is enhanced. The detection may therefore be more accurate and blood-sensitive in comparison to existing chromogenic material for litters. In an optional aspect, a perceptible coloration may appear when the chromogenic absorbent material is contacted with blood at a concentration of at least 100 red cells per μL in excretions (also referred to as blood concentration threshold). In an optional aspect, the chromogenic solution may have a concentration of oxidizing agent ranging between 0.1 wt % to 0.5 wt % (mass of oxidizing agent with respect to the total mass of the solution). The chromogenic solution may have a concentration of inclusion complex ranging between 1 wt % and 50 wt %. Preferably, the chromogenic solution may have a concentration of inclusion complex between 4 wt % and 25 wt %.

In another aspect, the present invention relates to a process for preparing a chromogenic solution for application in connection to the above-mentioned chromogenic absorbent material. The preparation process includes the following steps:
   preparation of a base solution by addition of a host compound into a solvent;
   addition of a chromogenic agent to the base solution so as to form a solvent-soluble inclusion complex including the host compound and the chromogenic agent as a guest compound associated with the host compound; and
   addition of an oxidizing agent to form the chromogenic solution, the oxidizing agent oxidizing the chromogenic agent in presence of peroxidatic/pseudoperoxidatic activity in excretions.

In an optional aspect, the chromogenic solution may include a ratio between 5 and 60 of total weight of host compound over total weight of chromogenic indicator. For example, the molar ratio of TMB over 2HPβCD, considering a molar mass of 1541 g/mol for the 2HPβCD, may be between 1/10 and 1/1. Preferably, this molar ratio may be between 1/7.5 and 1/1. Experiments have shown that a molar ratio of 1/1 rapidly produces a deep blue coloration of TMB when oxidized (cf. Example 3).

In an optional aspect, the process may include an addition of a buffering agent, a color enhancer, a stabilizer, an anti-metal agent or a combination thereof. The anti-metal agent may be used to precipitate metallic ions, such as ferric ions, that are possibly present in solution and avoid reaction with the chromogenic indicator.

In an optional aspect, the chromogenic solution may be prepared and tailored to the particular absorptive material.

In another aspect, the present invention relates to a process for manufacturing a chromogenic absorbent material as defined above. The manufacturing process includes combining an absorptive material with a chromogenic solution so as to form the chromogenic absorbent material. The absorptive material may be provided as a plurality of particles as defined above.

Figure 8:
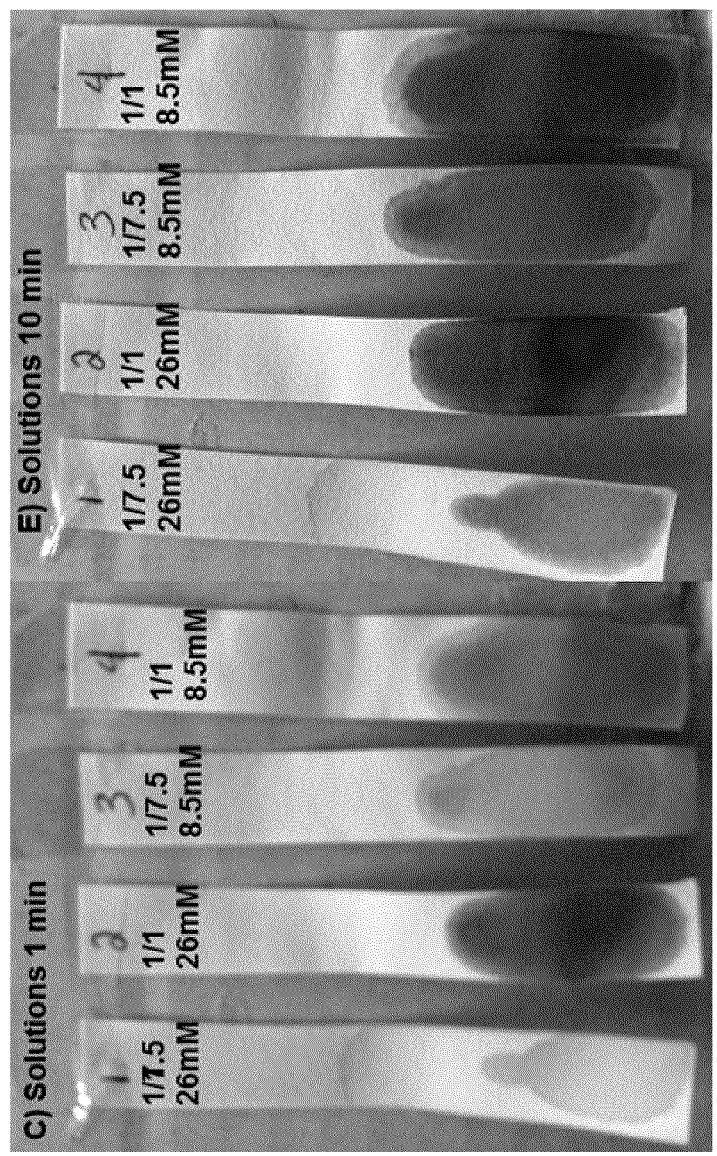
FIG. 8 is a photograph of chromogenic absorbent paper pieces soaked with different blood solutions.
Figure 9:
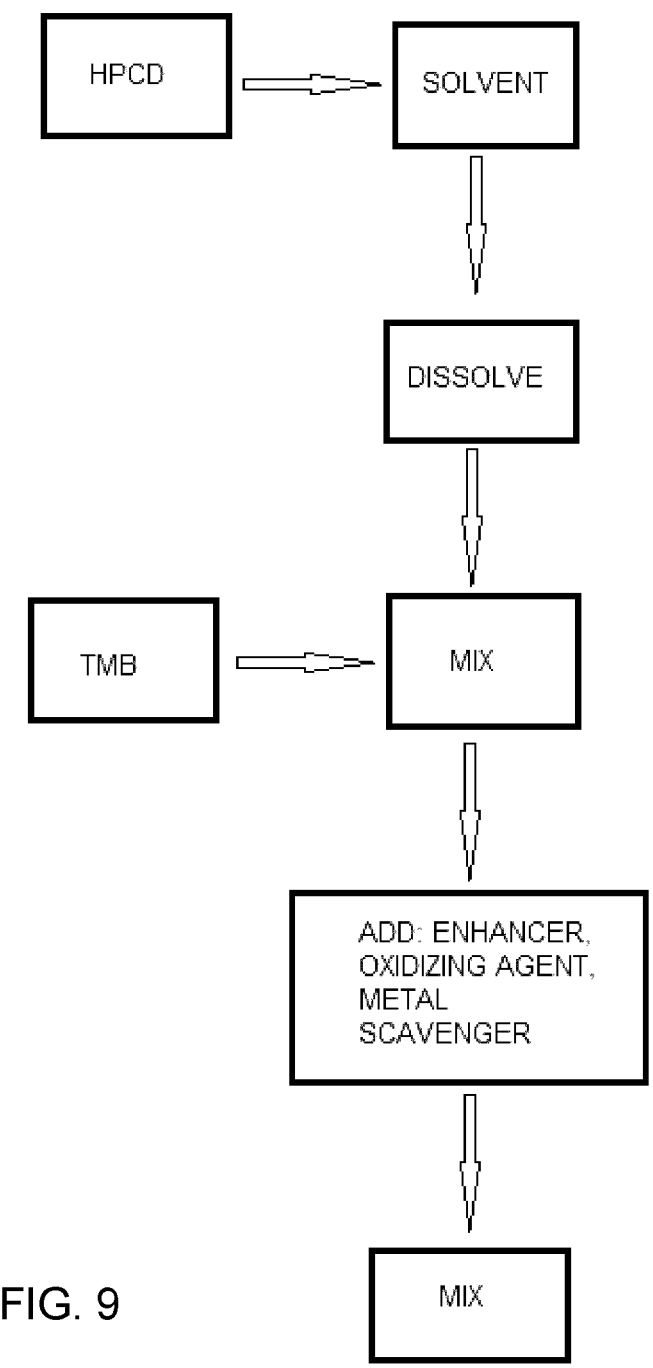
FIG. 9 is a schematic drawing of process steps for producing a chromogenic absorbent material.

Referring to FIG. 8, the process may include dissolving 2HPβCD in an aqueous solution so as to form a 2HPβCD solution. The process may further include dissolving TMB in the 2HPβCD solution so as to produce the chromogenic solution. After complete dissolution of TMB, various additives such as buffering agent, stabilizer, color enhancer, anti-dust agent or metal scavengers or a combination thereof may be added to the solution.

Optionally, the chromogenic solution may be sprayed onto a surface of the absorptive material. The spraying technique may be suited for absorptive material such as paper or perlite. Alternatively, the chromogenic solution may be added in a mixer to the particles of absorptive material for impregnation thereof.

In an optional aspect, the process may include the formation of the absorptive material before combination with the chromogenic solution. The absorptive material may be formed by extrusion, impregnation, pressure agglomeration or tumble growth agglomeration.

Optionally, the chromogenic solution may be added to a gelled absorptive material in an extruder. When used in combination to extruded material, the solution may be added in an early stage of the extrusion process during mixing of the components of the absorptive material at a temperature ranging from 70 to 80° C. Alternatively, when used in combination to extruded material, the solution may be added during final stage of extrusion when heat and shear treatment are minimized and the temperature is sufficiently low such that the chromogenic and oxidizing agent do not degrade or deactivate due to high temperature.

For example, the chromogenic solution may be injected at a point near the exit of the extruder such that the absorptive material has formed a gelled matrix and the components in the chromogenic solution are quickly dispersed within the gelled matrix prior to exiting the extruder.

Optionally, before exiting the extruder, the absorptive material may be injected with a gaseous stream so as to increase the porosity of the extruded particles and therefore increase their contact surface with excretions. One difficulty of the extruding technique, however, is that the process temperature can lead to the degradation or reaction of the oxidizing agent. Thus, for such embodiments, the absorptive material should be handled carefully at reduced temperatures, using stabilizing additives, or choosing oxidizing agents that do not react at the processing conditions, such that the oxidizing agents remain active in the final chromogenic absorbent material.

EXAMPLES

Example 1

Experiments have been performed by soaking paper solid matrix with 100 to 500 g of chromogenic solution per kilogram of paper. The chromogenic solution used for this purpose is detailed in Table 2:

TABLE 2

| Compound | Molar Mass (g/mol) | Concentration (mMol) | Ratio/ TMB(x) | Massic concentration (g/L) | % m/m |
|---|---|---|---|---|---|
| Water (solvent) | | | | 1000.00 | 74.27 |
| 2HPβCD (host compound) | 1541.00 | 200.00 | 7.5x | 308.20 | 22.89 |
| TMB (chromogenic indicator) | 240.34 | 26.67 | | 6.41 | 0.48 |
| Sodium citrate | 294.10 | 56.92 | | 16.74 | 1.24 |
| Citric acid (buffering agent) | 192.12 | 40.00 | | 7.68 | 0.57 |
| EDTA (stabilizer) | 372.24 | 4.00 | 0.15x | 1.49 | 0.11 |
| Cumene hydroperoxide (oxidizing agent) | 152.19 | 13.33 | 0.5x | 2.03 | 0.15 |
| Lepidine (color enhancer) | 143.19 | 26.67 | 1x | 3.82 | 0.28 |

Figure 6:
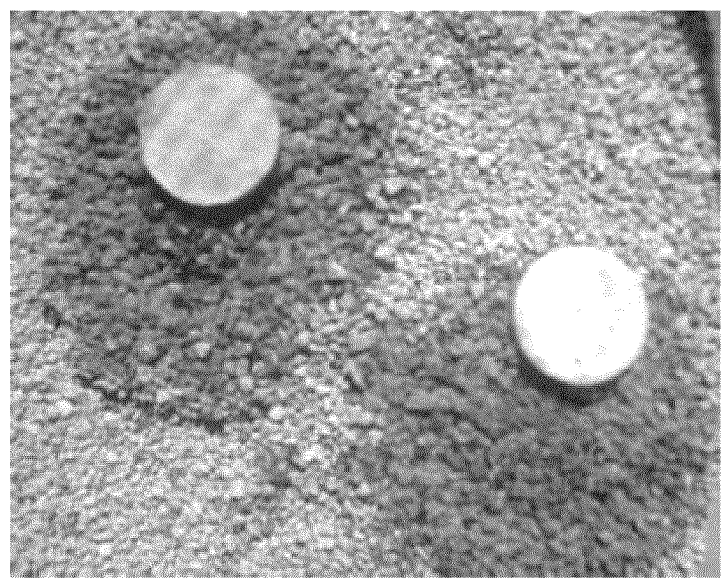
FIG. 6 is a photograph of a chromogenic absorbent material pieces soaked with urine.

FIG. 6 shows two particles of paper chromogenic absorbent material prepared with the above described chromogenic solution. The left particle has been contacted with urine including blood. Upon contact with blood, the chromogenic indicator included in the particle is oxidized and a blue coloration appears after 2 to 15 minutes. The final blue shade is obtained after 30 minutes. The right particle has been contacted with urine which does not include blood. No coloration is observed.

Example 2

Experiments have been performed by soaking extruded wheat starch pellets with an amount of aqueous solution having a 0.0215% concentration in blood, or with the same amount of synthetic urine. The wheat starch pellets were prepared by extruding wheat starch and injecting 0.28 kg of the chromogenic solution by kg of wheat starch at the beginning of the extrusion process.

Figure 7:
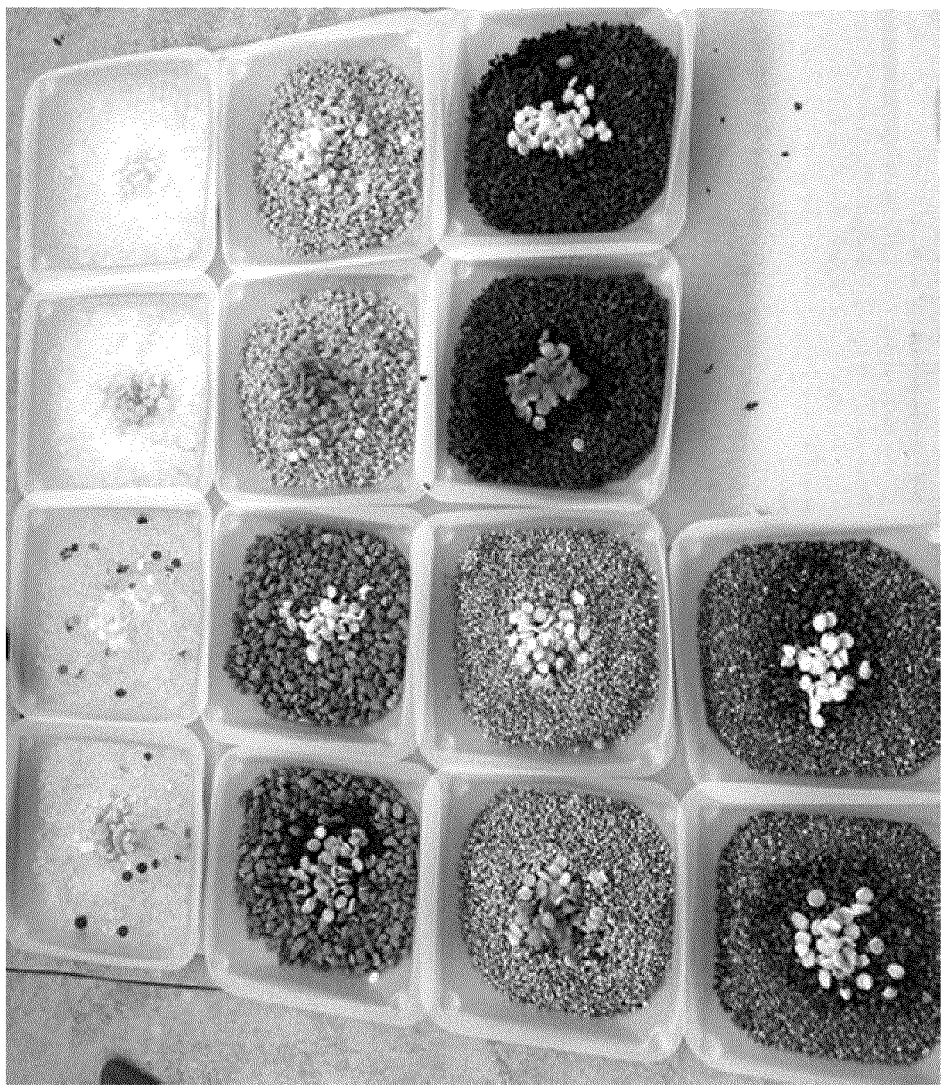
FIG. 7 is a photograph of a chromogenic absorbent wheat starch and paper material pieces soaked with blood solution and synthetic urine.

FIG. 7 illustrates that the pellets contacted with the blood solution (columns 1 and 3) and the synthetic urine (column 2 and 4) after 48 hours. The pellets contacted with the blood solution (columns 1 and 3) have a distinctive blue coloration whereas the pellets contacted with synthetic urine (columns 2 and 4) do not show any blue coloration.

Example 3

Experiments have been also been performed to evaluate the influence of the mass ratio TMB/2HPβCD on the blue coloration when substrate is contacted by blood solution. Four chromogenic solutions have been prepared with a ratio of 1/1 or 1/7.5 as indicated in Table 3. The molar concentrations and mass percentage of 2HPβCD and TMB in each of the four solutions are respectively given in Table 4 and Table 5. These chromogenic solutions were used to prepare chromogenic absorbent paper which was soaked with a 0.0215% blood solution.

TABLE 3

| CHROMOGENIC SOLUTION | RATIO TMB/2HPβCD |
|---|---|
| 1 | 1/7.5 |
| 2 | 1/1 |
| 3 | 1/7.5 |
| 4 | 1/1 |

TABLE 4

| Component | Water | 2HPβCD | TMB | Sodium citrate | Citric acid | Cumene hydroperoxide | Lepidine |
|---|---|---|---|---|---|---|---|
| Molar mass (g/mol) | 18.01 | 1541.00 | 240.34 | 294.10 | 192.12 | 152.19 | 143.19 |
| Concentration in solution 1 (mMol) | — | 200.00 | 26.67 | 56.92 | 40.00 | 13.33 | 26.67 |
| Concentration in solution 2 (mMol) | — | 26.67 | 26.67 | 56.92 | 40.00 | 13.33 | 26.67 |
| Concentration in solution 3 (mMol) | — | 63.75 | 8.50 | 56.92 | 40.00 | 4.25 | 8.50 |
| Concentration in solution 4 (mMol) | — | 8.50 | 8.50 | 56.92 | 40.00 | 4.25 | 8.50 |

TABLE 5

| Components (in molar mass percentage) | Solution 1 | Solution 2 | Solution 3 | Solution 4 |
| --- | --- | --- | --- | --- |
| Water | 74.27 | 92.66 | 88.65 | 95.89 |
| 2HPβCD | 22.89 | 3.81 | 8.71 | 1.26 |
| TMB | 0.48 | 0.59 | 0.18 | 0.20 |
| Sodium citrate | 1.24 | 1.55 | 1.48 | 1.60 |
| Citric acid | 0.57 | 0.71 | 0.68 | 0.74 |
| Cumene hydroperoxide | 0.15 | 0.19 | 0.06 | 0.06 |
| Lepidine | 0.28 | 0.35 | 0.11 | 0.12 |

FIG. 7 shows the four chromogenic absorbent papers soaked with the blood solution after 1 minute and after 10 minutes. After 10 minutes, a deep blue coloration is obtained for each paper for every ratio TMB/2HPβCD and TMB concentration. However, when comparing effects of solutions 1 and 2, FIG. 7 illustrates that, for the same concentration of TMB, a ratio TMB/2HPβCD of 1/1 enable obtaining a blue coloration more rapidly than a ratio of 1/7.5.

The invention claimed is:

1. A chromogenic absorbent material for an animal litter, the chromogenic absorbent material comprising:
   an absorptive material for absorbing an animal excretion;
   an oxidizing agent responsive to peroxidatic/pseudoperoxidatic activity in the animal excretion to provide oxidizing activity; and
   an inclusion complex including a host compound and a guest compound, the guest compound being a chromogenic indicator associated with the host compound and being chromogenically responsive to the oxidizing activity of the oxidizing agent.

2. The chromogenic absorbent material of claim 1, wherein the absorptive material comprises a polysaccharide.

3. The chromogenic absorbent material of claim 2, wherein the polysaccharide comprises starch, modified starch, amylopectin, modified amylopectin, amylose, modified amylose, cellulose or cellulosic fibers or a combination thereof.

4. The chromogenic absorbent material of claim 1, wherein the host compound comprises hydroxypropyl-alpha-cyclodextrin, 2-hydroxypropyl-beta-cyclodextrin, hydroxypropyl-gamma-cyclodextrin or a combination thereof.

5. The chromogenic absorbent material of claim 1, wherein the oxidizing agent comprises a hydroperoxide, a hydroperoxide precursor or a combination thereof.

6. The chromogenic absorbent material of claim 1, wherein the chromogenic indicator comprises a benzidine-type compound.

7. A chromogenic absorbent material for an animal litter, the chromogenic absorbent material comprising:
   an absorptive material comprising a first polysaccharide, for absorbing an animal excretion;
   a second polysaccharide comprising cellulose, cellulosic fibers, an oligosaccharide or a mixture thereof;
   an oxidizing agent responsive to peroxidatic/pseudoperoxidatic activity in the animal excretion to provide oxidizing activity; and
   a chromogenic indicator being chromogenically responsive to the oxidizing activity of the oxidizing agent;
   wherein the second polysaccharide and the chromogenic indicator form an inclusion complex.

8. The chromogenic absorbent material of claim 7, wherein the first polysaccharide comprises starch, modified starch, amylopectin, modified amylopectin, amylose, modified amylose or a combination thereof.

9. The chromogenic absorbent material of claim 7, wherein the first polysaccharide comprises pre-gelatinized starch, glass-like starch, waxy starch, anionic starch, cationic starch, fractionated starch, cross-linked starch, hydroxyalkylated starch, alkylated starch, or a mixture thereof.

10. The chromogenic absorbent material of claim 7, wherein the first polysaccharide comprises pre-gelatinized starch.

11. The chromogenic absorbent material of claim 7, wherein the second polysaccharide comprises cellulose.

12. The chromogenic absorbent material of claim 7, wherein the oligosaccharide comprises hydroxypropyl-alpha-cyclodextrin, 2-hydroxypropyl-beta-cyclodextrin, hydroxypropyl-gamma-cyclodextrin or a combination thereof.

13. The chromogenic absorbent material of claim 7, wherein the oxidizing agent comprises cumene hydroperoxide, diisopropylbenzene dihydroperoxide or a combination thereof.

14. The chromogenic absorbent material of claim 7, wherein the chromogenic indicator comprises a benzidine-type compound.

15. The chromogenic absorbent material of claim 14, wherein the benzidine-type compound comprises 3,3',5,5'-tetramethylbenzidine.

16. The chromogenic absorbent material of claim 7, further comprising a buffering agent, a stabilizer, a metal-scavenger agent, a color enhancer or a combination thereof.

17. The chromogenic absorbent material of claim 16, wherein the color enhancer comprises 6-methoxyquinoline, lepidin, phenol derivatives, nitrobenzene, N-methylpyrrolidone, ethylene carbonate or a combination thereof.

18. The chromogenic absorbent material of claim 16, wherein the stabilizer comprises ammonium molybdate, polyethylene glycol, polyvinylpyrrolidone, polyethylene oxide or derivatives thereof or a combination thereof.

19. Particles of the chromogenic absorbent material as defined in claim 7, the particles of the chromogenic absorbent material being used in combination with or as animal litter.

20. An animal litter material for detecting peroxidatic/pseudoperoxidatic activity in an animal excretion, the animal litter material comprising the chromogenic absorbent material as defined in claim 7.

21. The chromogenic absorbent material of claim 7, wherein the second polysaccharide has a frusto-conical configuration, and wherein the inner space of the frusto-conical configuration enables trapping and stabilizing of the chromogenic indicator.

* * * * *